(12) United States Patent
Sano

(10) Patent No.: US 7,892,168 B2
(45) Date of Patent: Feb. 22, 2011

(54) CONFOCAL ENDOSCOPE SYSTEM

(75) Inventor: Hiroshi Sano, Chiba (JP)

(73) Assignee: Hoya Corporation, Tokyo (JP)

( * ) Notice: Subject to any disclaimer, the term of this patent is extended or adjusted under 35 U.S.C. 154(b) by 993 days.

(21) Appl. No.: 11/696,316

(22) Filed: Apr. 4, 2007

(65) Prior Publication Data
US 2007/0236782 A1 Oct. 11, 2007

(30) Foreign Application Priority Data
Apr. 5, 2006 (JP) .............................. 2006-104029

(51) Int. Cl.
*A61B 1/06* (2006.01)
*A61B 1/04* (2006.01)
(52) U.S. Cl. ..................... 600/167; 600/160; 600/425; 600/109
(58) Field of Classification Search ................ 600/109, 600/160, 167, 168, 182, 425, 473; 359/368
See application file for complete search history.

(56) References Cited

U.S. PATENT DOCUMENTS

| | | | | |
|---|---|---|---|---|
| 5,633,675 | A | * | 5/1997 | Danna et al. .................. 348/65 |
| 6,224,542 | B1 | * | 5/2001 | Chang et al. ................. 600/109 |
| 6,839,586 | B2 | * | 1/2005 | Webb .......................... 600/478 |
| 2002/0026093 | A1 | * | 2/2002 | Ooyatsu ..................... 600/118 |
| 2004/0158129 | A1 | | 8/2004 | Okata et al. |
| 2004/0212808 | A1 | * | 10/2004 | Okawa et al. ............... 356/479 |
| 2004/0254474 | A1 | * | 12/2004 | Seibel et al. ................ 600/473 |
| 2005/0013478 | A1 | * | 1/2005 | Oba et al. ................... 382/154 |
| 2005/0052753 | A1 | * | 3/2005 | Kanai ......................... 359/642 |
| 2005/0059894 | A1 | * | 3/2005 | Zeng et al. .................. 600/476 |
| 2005/0280818 | A1 | * | 12/2005 | Yamashita et al. .......... 356/318 |

FOREIGN PATENT DOCUMENTS

JP 3396165 2/2003

OTHER PUBLICATIONS

English language Abstract and English language computer-generated translation of JP 11-318905 A, which corresponds to JP 3396165.

* cited by examiner

*Primary Examiner*—John P Leubecker
*Assistant Examiner*—Jeffrey H Chang
(74) *Attorney, Agent, or Firm*—Greenblum & Bernstein P.L.C.

(57) ABSTRACT

There is provided a confocal endoscope system which is provided with an electronic endoscope having a confocal optical unit configured to emit illumination light toward an object and to obtain only light from a certain point of the object, and a processor to which the light obtained by the confocal optical unit is inputted. The processor is provided with an image processing unit that generates image data representing an image of the object based on the light transmitted from the confocal optical unit, and a measuring information superimposing unit that generates composite image data representing a composite image generated by superimposing measuring information for measuring the object on the image generated by the image processing unit. The measuring information superimposing unit determines a display condition of the measuring information on the composite image in accordance with an imaging area of the confocal optical unit.

18 Claims, 5 Drawing Sheets

CONFOCAL ENDOSCOPE SYSTEM

BACKGROUND OF THE INVENTION

The present invention relates to a confocal endoscope system capable of obtaining an observation image through a confocal optical system.

Devices for medical diagnostic purposes configured to superimpose scale information for measuring an object on an observation image have been proposed. Such a device is provided with a probe to be inserted into a body cavity of a subject to obtain the observation image. For example, Japanese Patent Publication No. 3396165 (hereafter, referred to as JP3396165) discloses an ultrasonic diagnostic device capable of superimposing a scale on an image generated based on ultrasonic waves reflected from a body cavity.

Recently, a confocal endoscope system having a confocal optical system capable of generating an observation image having a resolution and a scaling factor higher than those of an observation image generated through a normal observation optical system has been proposed. More specifically, the confocal endoscope system is configured to illuminate tissue in a body cavity, to receive only part of light passing through a pinhole located at a position conjugate with a focal point of the confocal optical system, and to generate an image based on a signal having the amplitude corresponding to the intensity of the light received through the pinhole.

In addition, the confocal endoscope system is capable of shifting the focal point by a minute amount in a direction of an optical axis (i.e., in a direction of a depth of a region being observed) so that observation of tissue at a depth of up to 250 µm from a surface of the tissue can be achieved. There is a demand for three-dimensional representation of an image of the tissue within the illuminated area by combining a plurality of images obtained by shifting the focal point in the direction of the depth of the tissue.

To put the confocal endoscope system to practical use, it is preferable that the confocal endoscope system has a function of precisely measuring the size of tissue including a region predicted to be affected and a function of generating a cross sectional image of the tissue along a direction of a depth of the tissue so as to enable an operator to quickly and precisely locate the affected region from the observation image.

The configuration disclosed in JP3396165 can only be applied to the ultrasonic diagnostic device having a specific configuration, and therefore can not be applied to the confocal endoscope system capable of generating an observation image having a high resolution and a high scaling factor.

SUMMARY OF THE INVENTION

The present invention is advantageous in that it provides a confocal endoscope system capable of superimposing scale information for measuring an object on an observation image in such a manner that a display condition of the scale information matches a display mode of the observation image.

According to an aspect of the invention, there is provided a confocal endoscope system which is provided with an electronic endoscope having a confocal optical unit configured to emit illumination light toward an object and to obtain only light from a certain point of the object, and a processor to which the light obtained by the confocal optical unit is inputted. The processor is provided with an image processing unit that generates image data representing an image of the object based on the light transmitted from the confocal optical unit, and a measuring information superimposing unit that generates composite image data representing a composite image generated by superimposing measuring information for measuring the object on the image generated by the image processing unit. The measuring information superimposing unit determines a display condition of the measuring information on the composite image in accordance with an imaging area of the confocal optical unit.

With this configuration, it is possible to display the measuring information matching an object image having a high quality, on the image of the object generated by the image processing unit.

In at least one aspect, the display condition of the measuring information is determined based on magnification of the confocal optical unit and an image height on an imaging surface of the confocal optical unit.

In at least one aspect, the electronic endoscope further includes a driving unit that moves the confocal optical unit in a direction of an optical axis of the confocal optical unit; and a moving amount detection unit that detects a moving amount of the confocal optical unit. The image processing unit includes a three dimensional image generation unit that generates image data representing a three-dimensional image of the object based on image data representing two-dimensional images generated based on the light transmitted from the confocal optical unit and detection results of the moving amount detection unit.

In at least one aspect, the confocal endoscope system includes a depth setting unit configured to set a depth defining a size of the three-dimensional image in a depth direction in this case, the three dimensional image generation unit generates the image data representing the three-dimensional image such that the three-dimensional image has the depth set by the depth setting unit.

In at least one aspect, the image processing unit includes a sectional image generation unit that generates image data representing a cross-sectional image of the object based on the three-dimensional image generated by the three dimensional image generation unit.

In at least one aspect, the image processing unit includes a sectional image position setting unit that sets a position of the cross-sectional image to be generated by the sectional image generation unit.

In at least one aspect, wherein the processor further includes an output control unit that intervenes in image data transmission between the image processing unit and the measuring information superimposing unit to selectively send image data of one of images generated in the image processing unit.

In at least one aspect, the confocal endoscope system further includes an image selection unit configured to designate an image to be selected by the output control unit.

In at least one aspect, the confocal endoscope system further includes a scale indication setting unit configured to transmit a control signal representing whether the measuring information should be superimposed on the image generated by the image processing unit. In this case, the output control unit sends the image data generated by the image processing unit to the measuring information superimposing unit when the control signal from the scale indication setting unit represents that the measuring information should be superimposed, and outputs the image data generated by the image processing unit directly to a display device without sending the image data generated by the image processing unit to the measuring information superimposing unit when the control signal from the scale indication setting unit represents that the measuring information should not be superimposed.

In at least one aspect, the processor further includes a zooming unit that subjects the composite image data generated by the measuring information superimposing unit to a digital zooming process and outputs the composite image data which has been subjected to the digital zooming process.

In at least one aspect, the confocal endoscope system further includes a zooming factor setting unit configured to set a zooming factor to be used by the zooming unit in the digital zooming process.

In at least one aspect, the measuring information represents a measurement unit matching the zooming factor at which the composite image is scaled by the zooming unit.

In at least one aspect, the confocal endoscope system further includes a moving amount setting unit configured to set a moving amount of the confocal optical unit. In this case, the driving unit moves the confocal optical unit by the moving amount set by the moving amount setting unit.

In at least one aspect, the confocal endoscope system further includes a measuring information setting unit configured to allow an operator to input settings regarding a display style of the measuring information in the composite image. In this case, the measuring information superimposing unit superimposes the measuring information on the image generated by the image processing unit such that the measuring information is represented in the composite image in accordance with the settings inputted through the measuring information setting unit.

In at least one aspect, the measuring information includes scale data representing a scale for measuring the object.

In at least one aspect, the scale has a plurality of types of scale marks indicating different measurement units, and the plurality of types of scale marks have different lengths and thicknesses.

In at least one aspect, the measuring information includes grid data representing a grid for measuring the object.

In at least one aspect, the measuring information includes scale data representing at least one scale for measuring the object. In this case, the settings inputted through the measuring information setting unit includes at least one of settings regarding a number of scales to be provided in the composite image, settings regarding movement of the at least one scale, and settings regarding rotation of the at least one scale.

In at least one aspect, the confocal optical unit emits laser light and obtains only fluorescence generated at the certain point of the object In at least one aspect, the confocal optical unit is a scan type confocal optical unit configured to move the illumination light in two dimensions with respect to the object.

BRIEF DESCRIPTION OF THE ACCOMPANYING DRAWINGS

DETAILED DESCRIPTION OF THE EMBODIMENTS

Hereinafter, an embodiment according to the invention are described with reference to the accompanying drawings.

Figure 1:
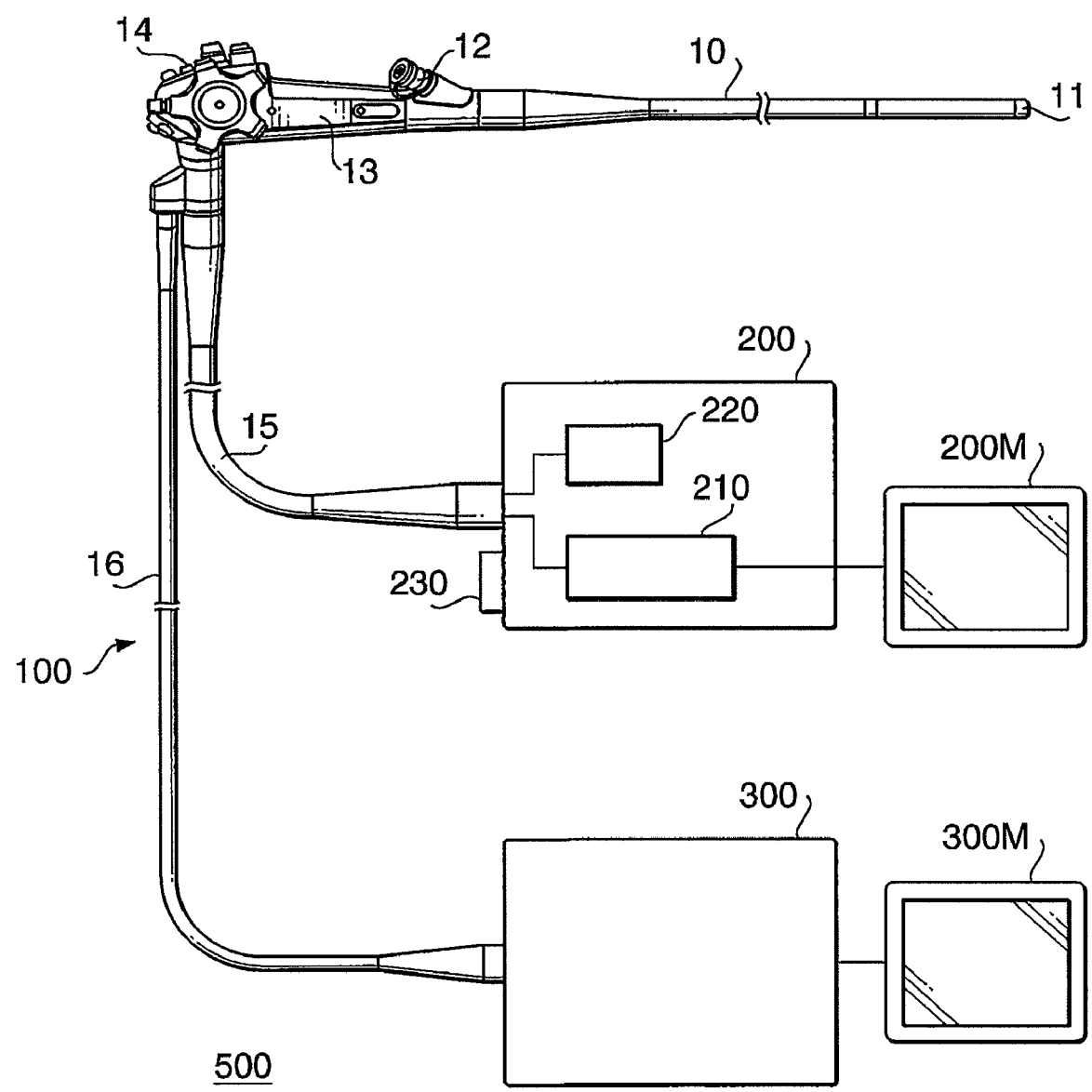
FIG. 1 is a block diagram of a confocal endoscope system according to an embodiment of the invention.

FIG. 1 is a block diagram of a confocal endoscope system 500 according to an embodiment of the invention. The confocal endoscope system 500 includes an electronic endoscope 100, a processor 200 to which the electronic endoscope 100 is connected, a processor 300 to which the electronic endoscope 100 is connected, and monitors 200M and 300M connected to the processors 200 and 300, respectively. The electronic endoscope 100 has a flexible insertion tube 10 to be inserted into a body cavity and is able to capture an image of tissue in the body cavity.

The electronic endoscope 100 has a normal observation function of capturing an image of the tissue through use of a solid-state image sensing device such as a CCD, and a confocal observation function of obtaining an image of the inside of the tissue through use of a confocal optical system. The electronic endoscope 100 includes the insertion tube 10, a tip portion 11, an instrument insertion hole 12 to which a treatment instrument such as a forceps is inserted, a holding unit 13 to be held by an operator to operate the electronic endoscope 100, an operation unit 14 to which various types of buttons and levers are provided for operation of the electronic endoscope 100 by the operator, and cables 15 and 16 to be connected to the processors 200 and 300, respectively.

The processor 200 is used for confocal observation. As shown in FIG. 1, the processor 200 includes an image processing unit 210, a light source 220 and an operation unit 230. The operation unit 230 includes, for example, various types of buttons or an external inputting device such as a keyboard and a mouse. The processor 300 is used for normal observation.

Figure 2:
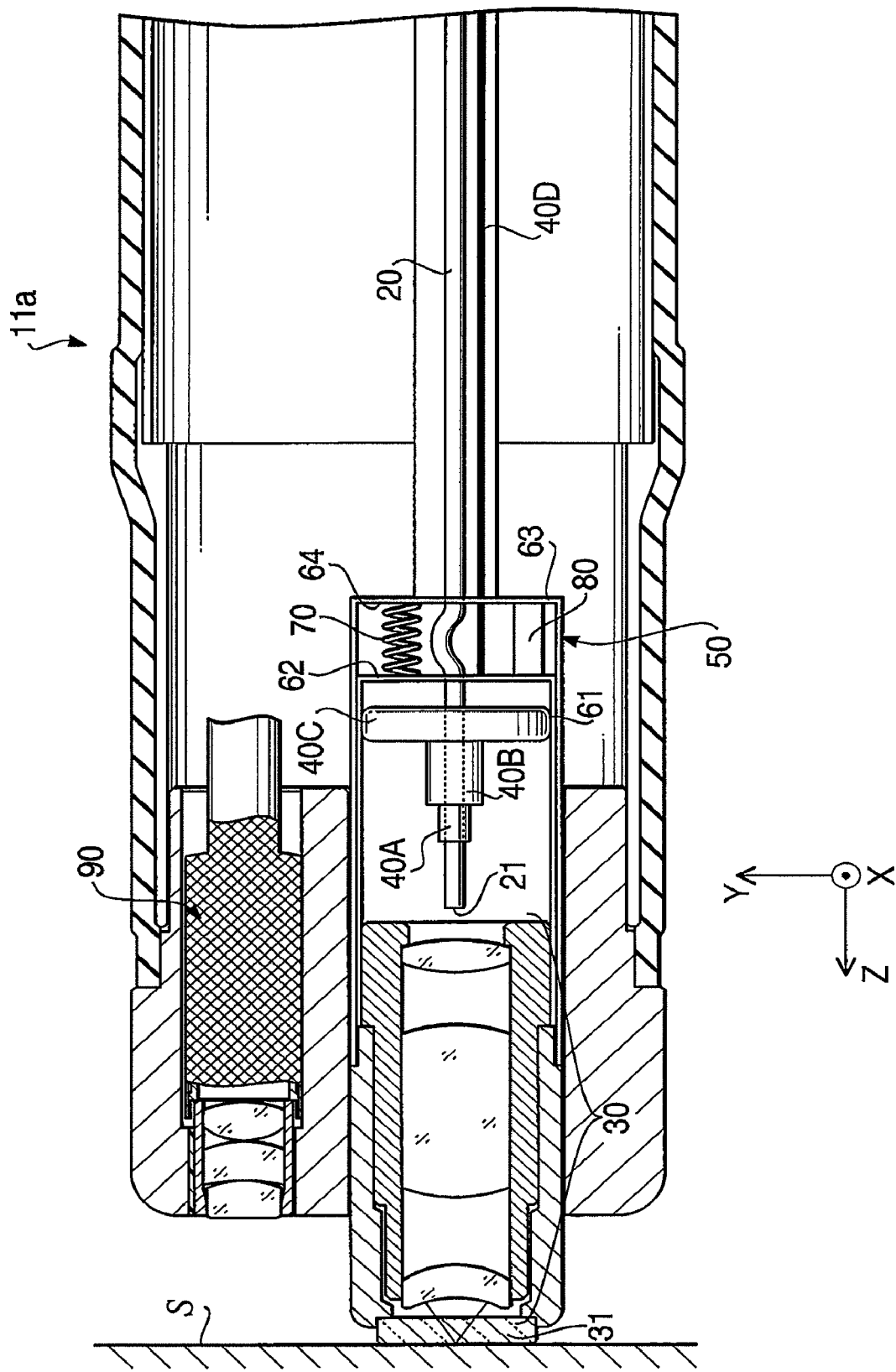
FIG. 2 is a cross-section of a part of an insertion tube illustrating an internal configuration of a tip portion of the insertion tube.

FIG. 2 is a cross-section of a part of the insertion tube 10 illustrating an internal configuration of the tip portion 11 of the insertion tube 10. The tip portion 11 includes a normal observation unit 90 and a confocal optical unit 50. The confocal optical unit 50 includes a single mode optical fiber (hereafter, simply referred to as an optical fiber) 20, an objective optical system 30, a cover glass 31, piezoelectric elements 40A and 40B, and a driving element 40C. The optical fiber 20, the objective optical system 30, the cover glass 31, the piezoelectric elements 40A and 40B are held in a cylindrical frame 61. The frame 61 is held in a cylindrical metal pipe 63 having a diameter slightly larger than that of the frame 61, so as to be slidable in the metal pipe 63.

In FIG. 2, a direction of an optical axis of the objective optical system 30 is defined as a direction of a Z-axis, X and Y axes are perpendicular to the Z-axis, and the X and Y axes which are orthogonal to each other define a plane (i.e., a X-Y plane) with which the optical axis perpendicularly intersects.

The optical fiber 20 serves as a light guide located between the objective optical system 30 and the light source 220 of the processor 200. The piezoelectric elements 40A and 40B are situated near an exit facet 21 of the optical fiber 20, and are respectively displaced by the piezoelectric effect in directions perpendicular to each other in the X-Y plane. The driving element 40C applies driving voltages to the piezoelectric elements 40A and 40B based on control signals transmitted thereto via a signal line 40D.

When driving voltages are applied to the piezoelectric elements 40A and 40B, the piezoelectric elements 40A and 40B respectively press a part of the optical fiber 20 near the exit facet 21 in the X-axis and Y-axis directions. With this configuration, the position of the exit facet 21 can be controlled to move in the X-Y plane. Although, strictly speaking, the locus of the exit facet 21 draws a curved surface having a center of curvature coinciding with an intersection of an extension of a chief ray of a beam emitted from the exit facet 21 and the optical axis, the curved surface drawn by the exit facet 21 is substantially equal to the X-Y plane because the moving amount of the exit facet 21 is extremely small. By the control of the position of the exit facet 21, the beam emitted from the exit facet 21 scans on a surface of tissue S in two dimensions. As described above, the confocal optical unit 50 is a scan type confocal optical unit.

Between an outer wall 62 of the frame 61 and an inner wall 64 of the metal pipe 63, a coil spring 70 and a shape-memory alloy 80 are mounted. Each of the outer wall 62 and the inner wall 64 is perpendicular to the Z-axis. The shape-memory alloy 80 has a function of being deformed by an external force at room temperature and shrinking to a memorized form when heated to a predetermined temperature or further. In this embodiment, the shape-memory alloy 80 shrinks in the Z-axis direction by heating. The coil spring 70 is attached to the outer wall 62 and the inner wall 64 in a compressed state with respect to a natural length. That is, in the state shown in FIG. 2, the coil spring 70 presses the frame 61 toward a tip end of the insertion tube 10.

As described above, when heated by an applied voltage, the shape-memory alloy 80 shrinks. The shrinking force of the shape-memory alloy 80 is designed to be larger than tension of the coil spring 70, so that the frame 61 slides toward a proximal end of the insertion tube 10 when the shape memory alloy 80 is heated. When the frame 61 slides in the Z-axis direction, a light convergence point of the objective optical system 30 also shifts in the Z-axis direction. Consequently, scanning of the light convergence point in the Z-axis direction can be achieved.

A process for generating observation images of the tissue S through use of the confocal optical system 50 will now be described. The optical fiber 20 guides the light emitted by the light source 220 into the inside of the electronic endoscope 100 so that the light is emitted from the exit facet 21. In this configuration, the exit facet 21 serves a point light source.

The beam emitted from the exit facet 21 passes through the objective optical system 30 and the cover glass 31, and converges onto the surface of the tissue S. As shown in FIG. 2, the cover glass 31 touches the surface of the tissue S. Since the beam (laser beam) emitted by the light source 220 includes a wavelength component functioning as excitation light, fluorescence produced in the tissue S by the excitation light returns while passing through the cover glass 31, the objective optical system 30 and the exit face in this order.

In this embodiment, the objective optical system 30 and the optical fiber 20 are located such that the exit facet 21 is located at a front focal point of the objective optical system 30. In other words, to the exit facet 21, only the fluorescence emitted from a point on the tissue S conjugate with the exit facet 21 enters. With this configuration, the exit facet 21 functions not only as a point source but also as a confocal pinhole that collects only the fluorescence from a light convergence point of the beam on the tissue S. As described above, the exit facet 21 (i.e., the point source) moves in the X-Y plane by the driving force of the piezoelectric elements 40A and 40B. The scanning of the light convergence point in the X-Y plane can be achieved.

The light (fluorescence) which entered the exit facet 21 is lead to the processor 200 via the optical fiber 20. The light returning to the processor 200 is separated from the light emitted by the light source 220, for example, by a fiber coupler, and is lead to the image processing unit 210. The image processing unit 210 forms point images respectively corresponding to the light convergence points scanned by the confocal optical unit 50 based on the light received from the confocal optical unit 50, and forms a frame of image (i.e., a still image) by arranging the point images at positions corresponding to the light convergence points scanned by the confocal optical unit 50.

The confocal endoscope system 500 supports a two-dimension display mode where an image of the tissue is displayed in two dimensions, a three-dimension display mode where an image of the tissue is displayed in three dimensions, and a section view mode where a cross sectional image of a position selected from the three dimensional image of the tissue is displayed. The image processing unit 210 performs image processing to display the processed image on the monitor 200M in one of the above mentioned display modes in accordance with an instruction inputted by the operator through the operation unit 230. The operator is able to conduct diagnosis on the tissue while viewing the displayed image having a high resolution and a high scaling factor.

The normal observation unit 90 includes an objective optical system through which the tissue S is illuminated with white light from the processor 300, and an image pickup device (not shown) which captures an image of the tissue S illuminated with the white light.

In normal observation, the tissue S is illuminated with the white light from the processor 300, and the light reflected from the tissue S is received by the image pickup device in the normal observation unit 90. The image pickup device transmits an image signal corresponding to the received light, to the processor 300. The processor 300 executes image processing on the received image signal to generate an image of the tissue, and displays the image on the monitor 300M.

Figure 3:
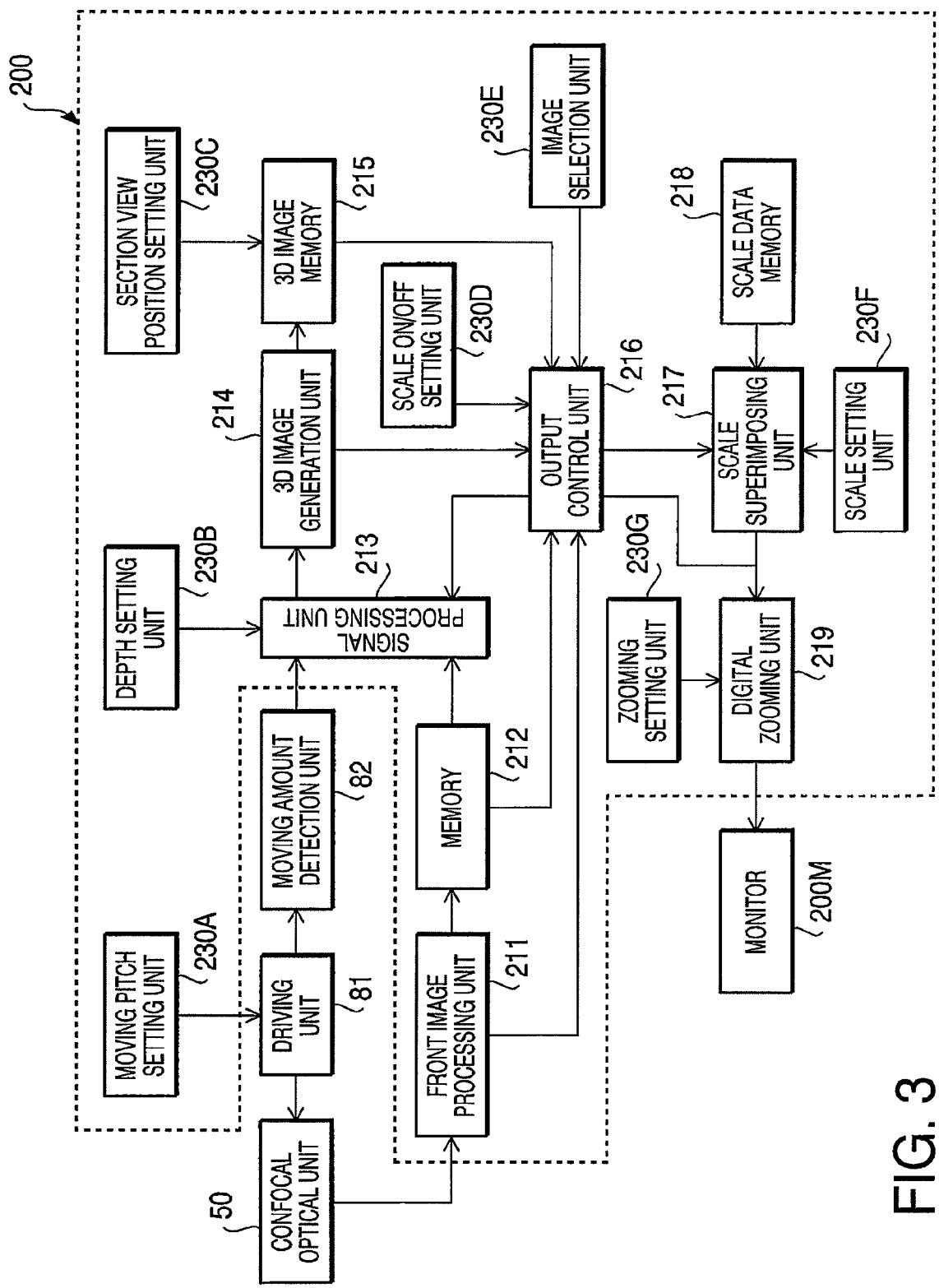
FIG. 3 is a block diagram implemented in the confocal endoscope system.

Hereafter, a scale display process for a confocal observation image is described. FIG. 3 is a block diagram for explaining the scale display process implemented in the confocal endoscope system 500. Processing units and memories 211 to 219 are implemented in the image processing unit 210, and setting units and selection units 230A to 230G are implemented in the operation unit 230.

First, the scale display process for a two-dimensional confocal observation image is described. The light returning from the confocal optical system 50 is received by an image sensor provided in a front image processing unit 211. In the front image processing unit 211, point images are formed in accordance with the light successively entering into the front image processing unit 211, and a frame of image (i.e., a two-dimensional image) is formed by arranging the point images at points corresponding to the light convergence points scanned by the confocal optical unit 50. The two-dimensional image is then stored temporarily in a memory 212 for two dimensional images.

An output control unit 216 controls the processing units in the image processing unit 210. The output control unit 216 switches between the display modes in accordance with a control signal from an image selection unit 230E which is operated by the operator. When the output control unit 216 receives a control signal instructing the output control unit to display images in the two-dimension display mode, the output control unit 216 reads a two dimensional image from the memory 212 in accordance with predetermined timing matching a period of a synchronizing signal for the monitor 200M, and sends the read two-dimensional image to a scale superimposing unit 217.

When the scale superimposing unit 217 receives the two-dimensional image from the output control unit 216, the scale superimposing unit 217 reads scale data from a scale data memory 218. Then, the scale superimposing unit 217 generates a composite image by superimposing a scale represented by the scale data on the two-dimensional image. The scale data is defined and stored in the scale data memory 218 in advance based on an imaging area of the confocal optical system 50. The scale superimposing unit 217 may be configured to define the scale data based on the imaging area of the confocal optical system 50 and to store the scale data in the scale data memory 218. The imaging area is defined by a magnification of the confocal optical system 50 and an image height on an imaging surface. Therefore, a scale superimposed on an observation image matches the size of an object displayed on the monitor 200M.

To the scale superimposing unit 217, a scale setting unit 230F forming the operation unit 230 is connected. By operating the scale setting unit 230F, the operator is able to set a display condition of the scale displayed on the observation image. For example, the position of the scale being displayed or the number of scales to be displayed can be changed.

The composite image generated by the above mentioned superimposing process is then inputted to a digital zooming unit 219. The digital zooming unit 219 executes a zooming process on the inputted composite image so that the composite image is scaled up or down to have a certain scaling factor set by the operator through a zooming setting unit 230G. The composite image outputted by the digital zooming unit 219 is then displayed on the monitor 200M. By thus subjecting the composite image, on which the scale has been superimposed, to the zooming process, the scale is also scaled up or down in response to the scale-up or scale-down of the object in the observation image. Therefore, precise measurement of the object can be achieved regardless of whether the zooming process is applied to the composite image.

Figure 4B:
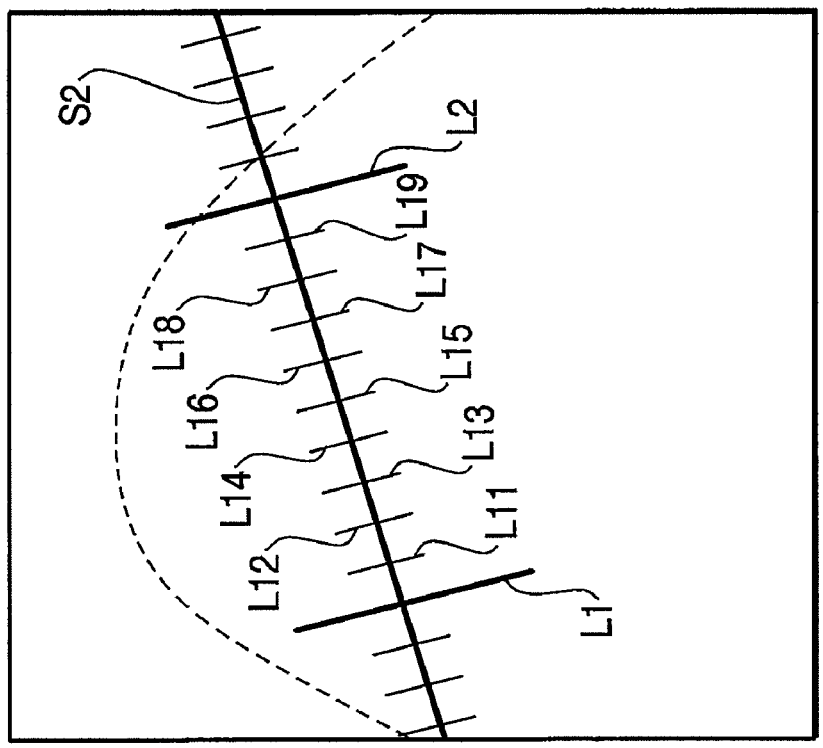
FIG. 4B shows a scale-up image of an object shown in FIG. 4A generated by a digital zooming process.
Figure 4A:
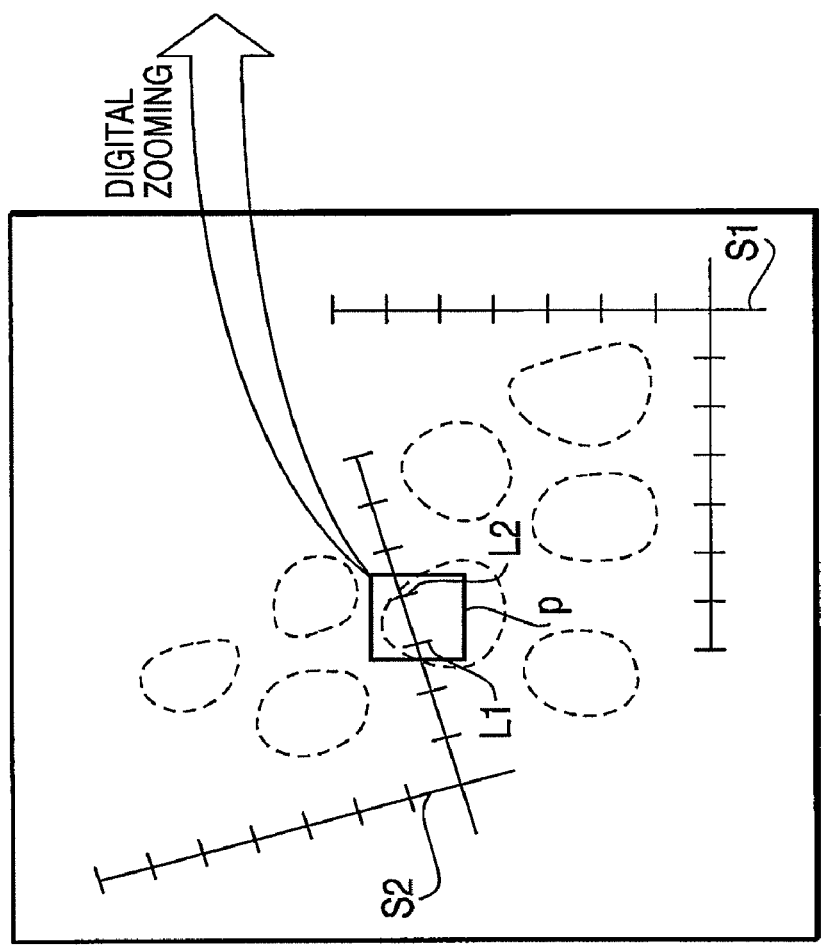
FIG. 4A is an example of a two-dimensional image on which scale information is superimposed through a scale display process.

FIG. 4A is an example of the two-dimensional observation image which has been subjected to the above mentioned scale display process. In the image shown in FIG. 4A, two scales S1 and S2 are displayed. Regarding the scales S1 and S2, the operator is able to move or rotate each of the scales by operating the scale setting unit 230F while viewing the two-dimensional observation image displayed on the monitor 200M. The operator is also able to change the number of scales to be displayed. For example, if a display condition of the scale S1 shown in FIG. 4A is defined as an initial condition, the scale S2 corresponds to a condition where the scale S1 has moved and rotated by operating the scale setting unit 230F.

Although in FIGS. 4A and 4B, each of the scales S1 and S2 is formed of two axes perpendicularly intersecting with each other, various types of scales may be used for the scales S1 and S2. For example, a scale formed of a single axis may be used.

In this embodiment, the scale displayed on the observation image has a plurality of types of scale marks. In order that suitable ones of the plurality of types of scale marks matching a zooming factor of an observation image are displayed, the scale data is configured such that the plurality of types of scale marks have the different lengths and thicknesses depending on measurement units of the scale. For example, the scale data is configured such that the scale mark representing a larger measurement unit has the longer and thicker line.

With this configuration, even if the scale marks for a small measurement unit are not recognizable when a scaling factor of an observation image is small, the scale marks for the small measurement unit becomes recognizable in accordance with the scale-up of the observation image (i.e., the scale marks for the small measurement unit are scaled up in accordance with the scale-up of the observation image). On the other hand, scale marks for a large measurement unit do not interfere the observation of the operator because the scale marks for the large measurement unit get out (i.e., are not superimposed on) of the observation image when the zooming factor of the observation image becomes high.

FIG. 4B shows a state where the zooming factor of the observation image shown in FIG. 4A is scaled up by the operator by operating the zooming setting unit 230G, and an area "p" of the observation image of FIG. 4A is scaled up. As described above, the scale data has various types of scale marks representing different measurement units. Therefore, strictly speaking, all of the various types of scale marks are simultaneously displayed on the observation image. However, since the length and thickness of the scale marks vary depending on measurement units of the scale, only suitable scale marks for a relatively large measurement unit (L1 and L2) are recognizable on the observation image shown in FIG. 4A. That is, the scale marks for measurement units smaller than the measurement unit of the scale marks L1 and L2 are not recognizable on the observation image shown in FIG. 4A.

On the other hand, when the zooming factor of the observation image is increased as shown in FIG. 4B, the scale marks are also scaled up, and thereby the scale marks L11 to L19 for the smaller measurement unit become recognizable.

Two different display states having different zooming factors shown in FIGS. 4A and 4B have been discussed for explaining the scale display process. However, the scale data may be configured to support more than two different types of scale marks. For example, the scale data may have scale marks representing a measurement unit smaller than that of the scale marks L11 to L19. In this case, when the zooming factor is increased from the display state of the observation image shown in FIG. 4B, the scale marks representing a measurement unit smaller than that for the scale marks L11 to L19 become recognizable.

In the above mentioned embodiment, the two-dimensional images generated by the front image processing unit 211 are stored in the memory 212. However, the two-dimensional image generated by the front image processing unit 211 may be directly transmitted to the output control unit 216 without being stored in the memory 212. In this case, it is possible to display images obtained by the confocal optical unit 50 in real time.

Hereafter, the scale display process for a three-dimensional confocal observation image is described. The shape-memory alloy 80 serving to move the confocal optical unit 50 in the Z-axis direction is controlled by a driving unit 81. More specifically, the driving unit 81 controls a moving amount of the confocal optical unit 50 in the Z-axis direction in accordance with pitch information inputted by the operator through a moving pitch setting unit 230A. If the pitch is set to a relatively small value, resolution of a three-dimensional image can be increased. If the pitch is set to a relatively larger value, data amount used for generating the three-dimensional image can be decreased, and therefore the processing speed of the scale display process can be increased.

The moving amount of the confocal optical unit 50 is detected by a moving amount detection unit 82. The moving amount detection unit 82 detects the moving amount of the confocal optical unit 50, for example, by detecting change of resistance, and sends a detection signal representing a detection result of the moving amount to a signal processing unit 213. The signal processing unit 213 generates position information representing a current position of the confocal optical unit 50 based on the detection signal from the moving amount detection unit 82. Then, the signal processing unit 213 reads a two-dimensional image temporarily stored in the memory 212, and associates the position information representing a current position of the confocal optical unit 50 with the two-dimensional image.

To the signal processing unit 213, a depth setting unit 230B is connected. The depth setting unit 230B is operated by the operator to set the size of a three-dimensional image in a depth direction (i.e., the depth of the three-dimensional image). The signal processing unit 213 associates the position information representing the current position of the confocal optical unit 50 with each two-dimensional image within the depth set by the operator through the depth setting unit 230B.

The output control unit 216 sends a control signal to the signal processing unit 213 when the output control unit 216 receives a control signal representing selection of a three-dimensional image from the image selection unit 230E. When receiving the control signal, the image processing unit 213 successively sends two-dimensional images with which the position information is associated, to a 3D (three-dimensional) image generation unit 214.

The 3D image generation unit 214 generates a three-dimensional image based on two-dimensional images which are successively inputted thereto and are associated with the position information. Then, the 3D image generation unit 214 stores the three-dimensional image in a memory provided in the 3D image generation unit 214. Subsequently, the three-dimensional image is stored in a 3D (three dimensional) image memory 215.

The output control unit 216 reads the three-dimensional image from the 3D image memory 215 at predetermined timing, and sends the three-dimensional image to the scale superimposing unit 217. The scale superimposing unit 217 superimposes the scale data on the three-dimensional image as in the case of the scale display process for the two-dimensional image. The output control unit 216 obtains scale data, from the scale data memory 218, representing a scale matching a display state of the three-dimensional image. That is, the scale data obtained by the output control unit 216 for the three-dimensional image is different from the above mentioned scale data for the two-dimensional image.

The three-dimensional image on which the scale has been superimposed is then subjected to the zooming process in the digital zooming unit 219. Then, the three dimensional observation image on which the scale is superimposed is displayed on the monitor 200M.

Figure 5:
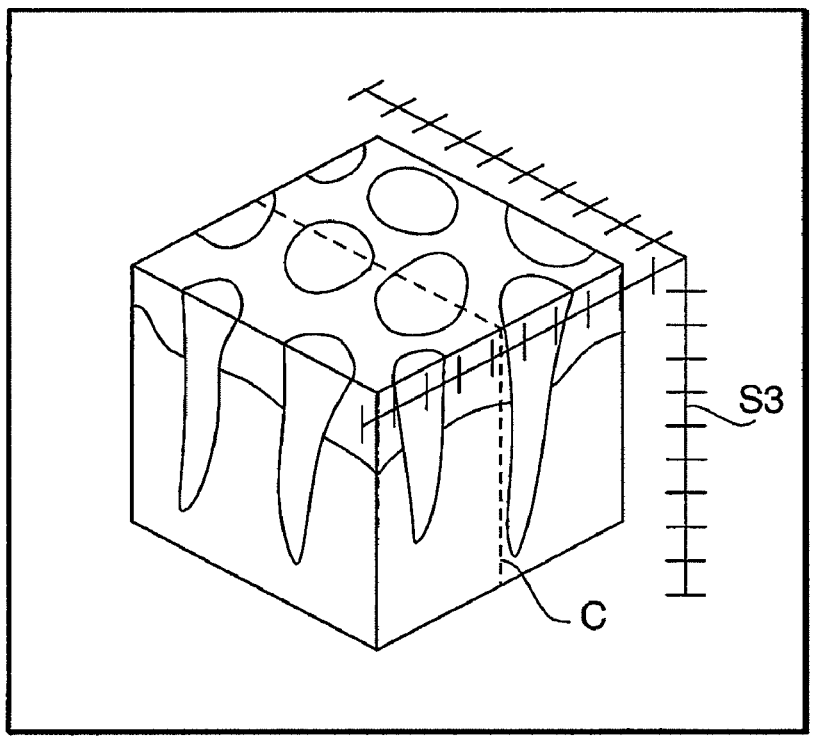
FIG. 5 is an example of a three-dimensional image on which scale information is superimposed through the scale display process.

FIG. 5 is an example of a three-dimensional observation image generated through the above mentioned image processing. On the three dimensional image shown in FIG. 5, a scale S3 is superimposed. As in the case of the scales S1 and S2 for the two-dimensional image, the operator is able to move and rotate the position of the scale S3. The number of scales to be displayed can also be changed by operating the scale setting unit 230F. Although the scale S3 is formed of three axes perpendicularly intersecting with each other, various types of scales suitable for measurement of the tissue may be superimposed on the three-dimensional image. For example, a scale formed of a single line or two lines may be superimposed for the measurement of the tissue.

By operating the image selection unit 230E, the operator is able to instruct the processor 200 to display a cross sectional image of the tissue at a desired position.

In order to display a cross sectional image of the displayed tissue, the operator conducts a setting operation as to which part of the tissue is to be displayed as a section view by operating a section view position setting unit 230C as well as operating the image selection unit 230E. More specifically, when receiving a control signal instructing selection of a section view from the image selection unit 230E, the output control unit 216 operates to display a mark C (formed by a dashed line) representing a position of a cross sectional image to be displayed. The position of the mark C can be adjusted by operating the section view position setting unit 230C.

The section view position setting unit 230C sends a signal representing a position of a cross sectional image to be displayed, to the 3D image memory 215. After receiving the signal from the section view position setting unit 230C, the 3D image memory 215 selects a cross sectional image indicated by the signal from the section view position setting unit 230C, and sends the selected cross sectional image to the output control unit 216.

The output control unit 216 sends the cross sectional image to the scale superimposing unit 217 in synchronization with predetermined timing matching the period of the synchronization signal for the monitor 200M. The scale superimposing unit 217 subjects the cross sectional image to the above mentioned scale display process.

Figure 6:
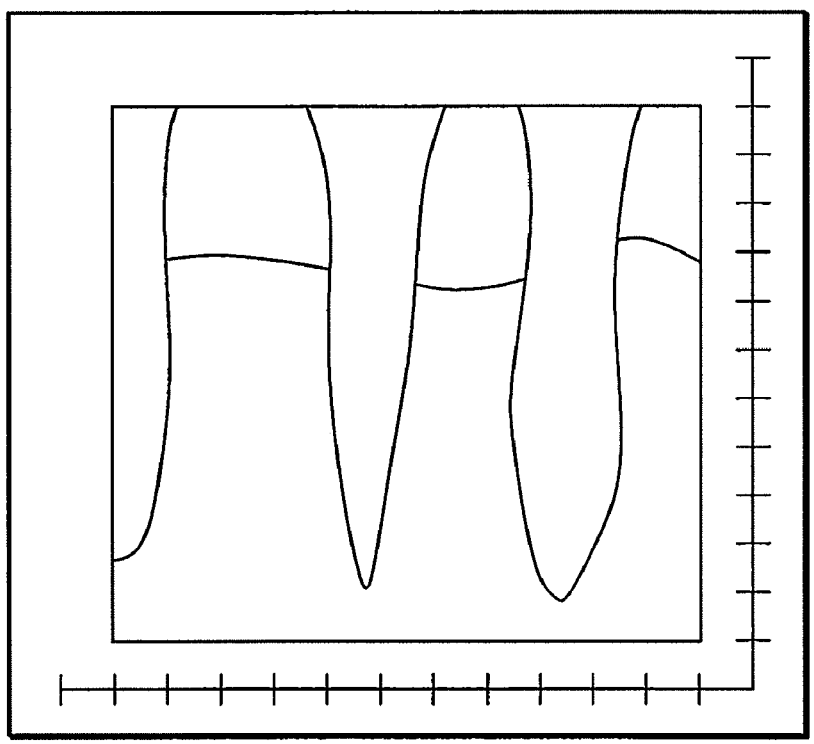
FIG. 6 shows an example of a cross sectional image on which scale information is superimposed through the scale display process.

The cross sectional image on which the scale has been superimposed is then subjected to the zooming process in the digital zooming unit 219, and is displayed on the monitor 200M. FIG. 6 shows an example of a cross sectional image displayed on the monitor 200M. The processor 200 may display both the three-dimensional object shown in FIG. 5 and the cross sectional image shown in FIG. 6 on the monitor 200 simultaneously.

The above mentioned scale display process is executed when execution of the scale display process is enabled by the operator through a scale on/off setting unit 230D. When the execution of the scale display process is disabled, the output control unit 216 directly sends an image selected by the operator through the image selection unit 230E to the digital zooming unit 219. In this case, no scale is superimposed on an observation image.

As described above, according to the embodiment, it is possible to display measuring information, such as a scale or a grid, matching an object image having a high quality, on the object image of the object generated by the front image processing unit 211. It is also possible to display measuring information matching the current display mode (the two-dimensional image display mode, the three dimensional image display mode, or the section view mode) of the object.

Although the present invention has been described in considerable detail with reference to certain preferred embodiments thereof, other embodiments are possible.

In the above mentioned embodiment, a scale formed of two or three axes are displayed as measuring information for measuring a displayed object. However, a grid formed of minute rectangles may be used as the measuring information.

A scan type confocal optical unit is employed as the confocal optical unit 50 in the above mentioned embodiment. However, a confocal optical unit configured to have another scanning scheme may be employed in the confocal endoscope system 500. For example, a confocal optical unit configured to have a two-dimensional array of optical fibers used for scanning an object may be employed in place of the scan type confocal optical unit.

In the above mentioned embodiment, the confocal endoscope system 500 is configured to emit the laser beam serving as excitation light and to obtain a confocal observation image based on the fluorescence generated in the tissue. However, the confocal endoscope system 500 may be configured to illuminate the tissue with normal light (e.g., white light) and to generate a confocal observation image from the light reflected from the tissue.

This application claims priority of Japanese Patent Application No. P2006-104029, filed on Apr. 5, 2006. The entire subject matter of the application is incorporated herein by reference.

What is claimed is:

1. A confocal endoscope system, comprising:
   an electronic endoscope having a confocal optical unit configured to emit illumination light toward an object and to obtain only light from a certain point of the object; and
   a processor to which the light obtained by the confocal optical unit is inputted,
   the processor comprising:
   an image processing unit that generates image data representing an image of the object based on the light transmitted from the confocal optical unit;
   a measuring information superimposing unit that generates composite image data representing a composite image generated by superimposing measuring information for measuring the object on the image generated by the image processing unit, the measuring information superimposing unit determining a display condition of the measuring information on the composite image in accordance with an imaging area of the confocal optical unit; and
   an output control unit that intervenes in image data transmission between the image processing unit and the measuring information superimposing unit to selectively send the image data representing the image generated by the image processing unit, and
   the confocal endoscope system further comprising:
   a scale indication setting unit configured to transmit a control signal representing whether the measuring information should be superimposed on the image generated by the image processing unit, and
   wherein the output control unit sends the image data generated by the image processing unit to the measuring information superimposing unit when the control signal from the scale indication setting unit represents that the measuring information should be superimposed, and outputs the image data generated by the image processing unit directly to a display device without sending the image data generated by the image processing unit to the measuring information superimposing unit when the control signal from the scale indication setting unit represents that the measuring information should not be superimposed.

2. The confocal endoscope system according to claim 1, wherein the display condition of the measuring information is determined based on magnification of the confocal optical unit and an image height on an imaging surface of the confocal optical unit.

3. The confocal endoscope system according to claim 1, wherein
   the electronic endoscope further comprises:
   a driving unit that moves the confocal optical unit in a direction of an optical axis of the confocal optical unit; and
   a moving amount detection unit that detects a moving amount of the confocal optical unit,
   wherein the image processing unit includes:
   a three dimensional image generation unit that generates image data representing a three-dimensional image of the object based on image data representing two-dimensional images generated based on the light transmitted from the confocal optical unit and detection results of the moving amount detection unit.

4. The confocal endoscope system according to claim 3, further comprising:
   a depth setting unit configured to set a depth defining a size of the three-dimensional image in a depth direction,
   wherein the three dimensional image generation unit generates the image data representing the three-dimensional image such that the three-dimensional image has the depth set by the depth setting unit.

5. The confocal endoscope system according to claim 3, wherein the image processing unit includes:
   a sectional image generation unit that generates image data representing a cross-sectional image of the object based on the three-dimensional image generated by the three dimensional image generation unit.

6. The confocal endoscope system according to claim 5, wherein the image processing unit includes:
   a sectional image position setting unit that sets a position of the cross-sectional image to be generated by the sectional image generation unit.

7. The confocal endoscope system according to claim 3, further comprising:
   a moving amount setting unit configured to set a moving amount of the confocal optical unit,
   wherein the driving unit moves the confocal optical unit by the moving amount set by the moving amount setting unit.

8. The confocal endoscope system according to claim 1, further comprising:
   an image selection unit configured to designate an image to be selected by the output control unit.

9. The confocal endoscope system according to claim 1, wherein the processor further comprises:
   a zooming unit that subjects the composite image data generated by the measuring information superimposing unit to a digital zooming process and outputs the composite image data which has been subjected to the digital zooming process.

10. The confocal endoscope system according to claim 9, further comprising a zooming factor setting unit configured to set a zooming factor to be used by the zooming unit in the digital zooming process.

11. The confocal endoscope system according to claim 9, wherein the measuring information represents a measurement unit matching the zooming factor at which the composite image is scaled by the zooming unit.

12. The confocal endoscope system according to claim 1, further comprising:
   a measuring information setting unit configured to allow an operator to input settings regarding a display style of the measuring information in the composite image,
   wherein the measuring information superimposing unit superimposes the measuring information on the image generated by the image processing unit such that the measuring information is represented in the composite image in accordance with the settings inputted through the measuring information setting unit.

13. The confocal endoscope system according to claim 12, wherein:
   the measuring information includes scale data representing at least one scale for measuring the object; and
   the settings inputted through the measuring information setting unit includes at least one of settings regarding a number of scales to be provided in the composite image, settings regarding movement of the at least one scale, and settings regarding rotation of the at least one scale.

14. The confocal endoscope system according to claim 1, wherein the measuring information includes scale data representing a scale for measuring the object.

15. The confocal endoscope system according to claim 14, wherein:
- the scale has a plurality of types of scale marks indicating different measurement units; and
- the plurality of types of scale marks have different lengths and thicknesses.

16. The confocal endoscope system according to claim 1, wherein the measuring information includes grid data representing a grid for measuring the object.

17. The confocal endoscope system according to claim 1, wherein the confocal optical unit emits laser light and obtains only fluorescence generated at the certain point of the object.

18. The confocal endoscope system according to claim 1, wherein the confocal optical unit is a scan type confocal optical unit configured to move the illumination light in two dimensions with respect to the object.

* * * * *